United States Patent
Tansey, Jr. et al.

(10) Patent No.: US 6,776,774 B2
(45) Date of Patent: *Aug. 17, 2004

(54) HEMOSTASIS GASKET VALVE

(75) Inventors: William J. Tansey, Jr., Ballston Spa, NY (US); Mark H. Van Diver, Argyle, NY (US); Eric Houde, Saratoga Springs, NY (US)

(73) Assignee: SciMed Life Systems, Inc., Maple Grove, MN (US)

( * ) Notice: Subject to any disclaimer, the term of this patent is extended or adjusted under 35 U.S.C. 154(b) by 274 days.

This patent is subject to a terminal disclaimer.

(21) Appl. No.: 09/906,376

(22) Filed: Jul. 16, 2001

(65) Prior Publication Data

US 2003/0014015 A1 Jan. 16, 2003

(51) Int. Cl.⁷ .......................................... A61M 5/178
(52) U.S. Cl. ........................... 604/167.04; 604/167.01; 604/256
(58) Field of Search .................. 604/167.01–167.04, 604/256, 246, 247, 523

(56) References Cited

U.S. PATENT DOCUMENTS

| 4,000,739 A | 1/1977 | Stevens .................... 128/214.4 |
| 4,254,773 A | 3/1981 | Waldbillig .................. 128/348 |
| 4,366,817 A | 1/1983 | Thomas ....................... 604/174 |
| 4,424,833 A | 1/1984 | Spector et al. .............. 137/849 |
| 4,430,081 A | 2/1984 | Timmermans .............. 604/256 |
| 4,436,519 A | 3/1984 | O'Neill ....................... 604/175 |
| 4,798,594 A | 1/1989 | Hillstead .................... 604/167 |
| 4,874,378 A | 10/1989 | Hillstead .................... 604/167 |
| 4,895,565 A | 1/1990 | Hillstead .................... 604/167 |
| 4,909,798 A | 3/1990 | Fleischhacker et al. ..... 604/256 |
| 4,929,235 A | 5/1990 | Merry et al. ................ 604/167 |
| 4,944,729 A | 7/1990 | Buckberg et al. ........... 604/164 |
| 4,946,133 A | 8/1990 | Johnson et al. .......... 251/149.1 |
| 4,950,257 A | 8/1990 | Hibbs et al. ................ 604/265 |
| 5,000,745 A | 3/1991 | Guest et al. ................ 604/256 |

(List continued on next page.)

FOREIGN PATENT DOCUMENTS

| EP | 0 344 907 A2 | 12/1989 |
| EP | 0 369 314 A2 | 5/1990 |
| EP | 0 442 194 A2 | 9/1991 |
| EP | 0 692 278 A1 | 1/1996 |
| WO | WO 99/06099 | 2/1999 |
| WO | WO 99/34849 | 7/1999 |
| WO | WO 01/17586 | 3/2001 |

OTHER PUBLICATIONS

US 5,520,663, 5/1996, Patterson et al. (withdrawn)
Brochure, "Pinnacle Introducer Sheaths" dated on or before Jul. 16, 2001, 3 sheets.

Primary Examiner—Thor Campbell
(74) Attorney, Agent, or Firm—Crompton, Seager & Tufte, LLC

(57) ABSTRACT

An improved vascular introducer sheath having a hemostasis valve assembly which provides tailored distribution of compressive forces along one of the top and bottom edges of each slit to avoid puckering of the slit(s) and to provide balanced performance in terms of bi-directional sealing effectiveness and device movement therethrough.

19 Claims, 5 Drawing Sheets

U.S. PATENT DOCUMENTS

| | | | | |
|---|---|---|---|---|
| 5,045,065 | A | 9/1991 | Raulerson | 604/167 |
| 5,059,186 | A | 10/1991 | Yamamoto et al. | 604/280 |
| 5,092,857 | A | 3/1992 | Fleischhacker | 604/256 |
| 5,098,393 | A | 3/1992 | Amplatz et al. | 604/167 |
| 5,114,408 | A | 5/1992 | Fleischhaker et al. | 604/167 |
| 5,137,519 | A | 8/1992 | Littrell et al. | 604/174 |
| 5,154,701 | A | 10/1992 | Cheer et al. | 604/167 |
| 5,167,637 | A | 12/1992 | Okada et al. | 604/167 |
| 5,188,607 | A | 2/1993 | Wu | 604/167 |
| 5,234,410 | A | 8/1993 | Graham et al. | 604/167 |
| 5,242,410 | A | 9/1993 | Melker | 604/164 |
| 5,242,413 | A | 9/1993 | Heiliger | 604/167 |
| 5,267,966 | A | 12/1993 | Paul | 604/167 |
| 5,295,657 | A | 3/1994 | Atkinson | 251/149.1 |
| 5,300,033 | A | 4/1994 | Miller | 604/167 |
| 5,330,435 | A | 7/1994 | Vaillancourt | 604/167 |
| 5,350,363 | A | 9/1994 | Goode et al. | 604/167 |
| 5,402,982 | A | 4/1995 | Atkinson et al. | 251/149.1 |
| 5,453,095 | A | 9/1995 | Davila et al. | 604/167 |
| 5,499,975 | A | 3/1996 | Cope et al. | 604/165 |
| 5,520,655 | A | 5/1996 | Davila et al. | 604/167 |
| 5,538,505 | A | 7/1996 | Weinstein et al. | 604/167 |
| 5,549,576 | A | 8/1996 | Patterson et al. | 604/247 |
| 5,613,956 | A | 3/1997 | Patterson et al. | 604/256 |
| 5,762,630 | A | 6/1998 | Bley et al. | 604/164 |
| 5,807,350 | A | 9/1998 | Diaz | 604/256 |
| 5,843,031 | A | 12/1998 | Hermann et al. | 604/95 |
| 5,911,710 | A | 6/1999 | Barry et al. | 604/249 |
| 5,944,697 | A | 8/1999 | Biche | 604/174 |
| 6,322,541 | B2 * | 11/2001 | West et al. | 604/256 |

* cited by examiner

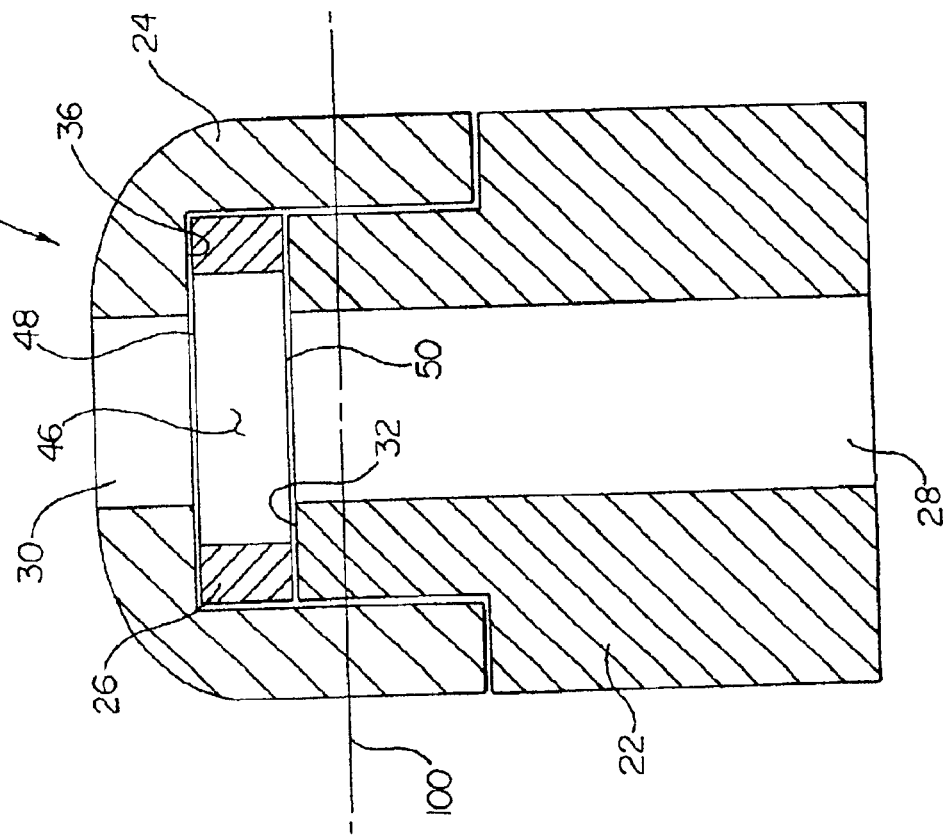
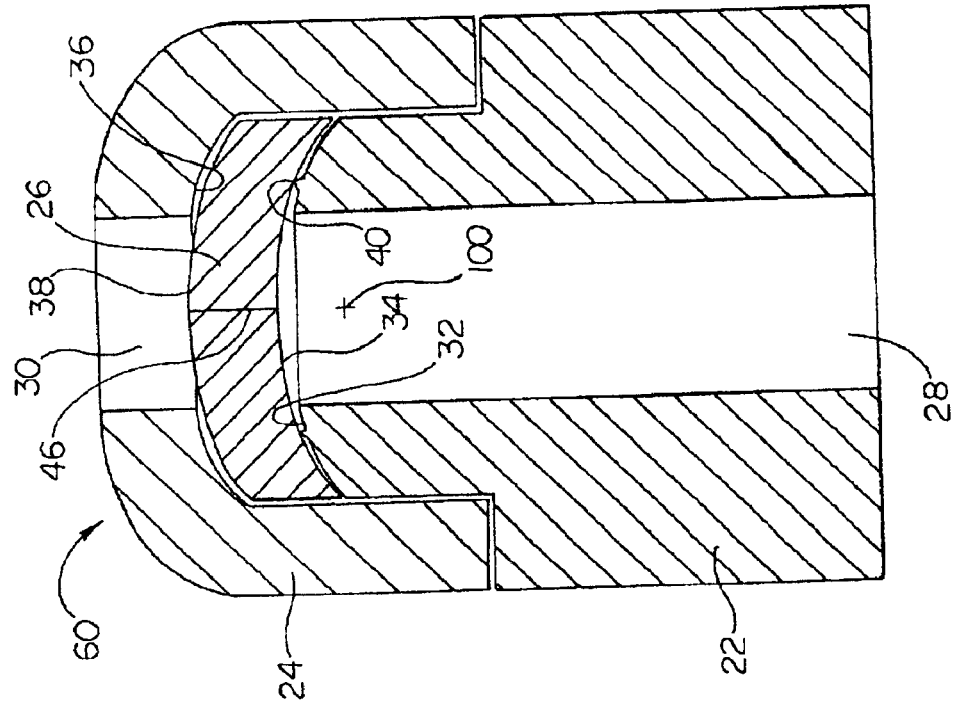

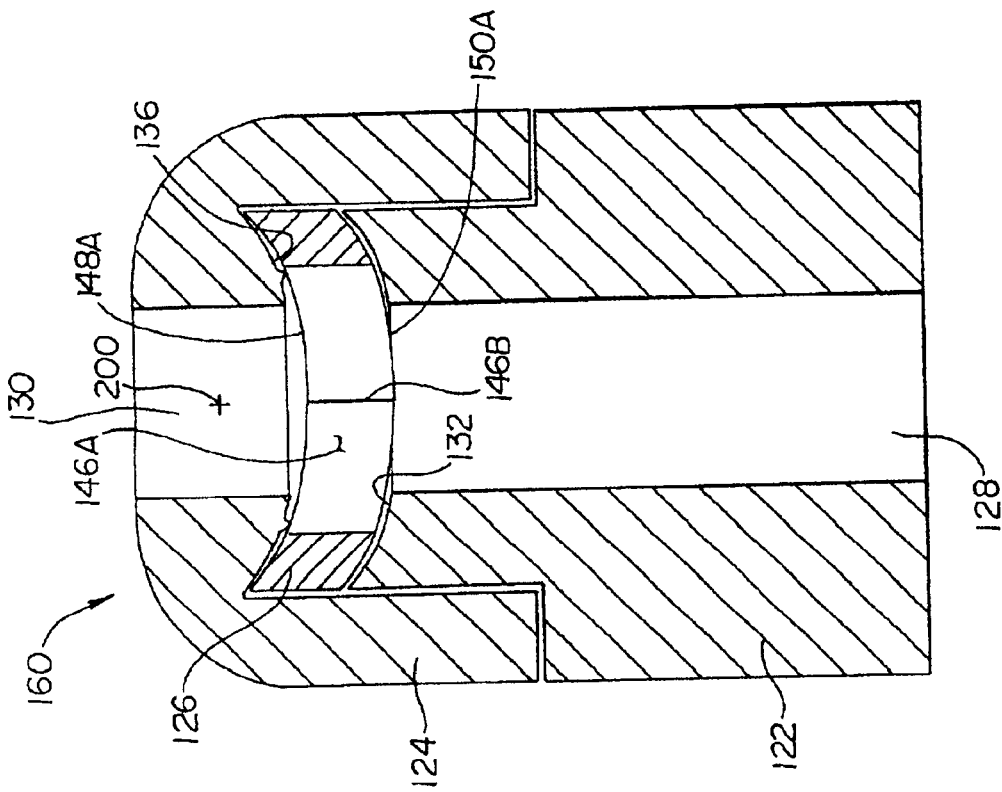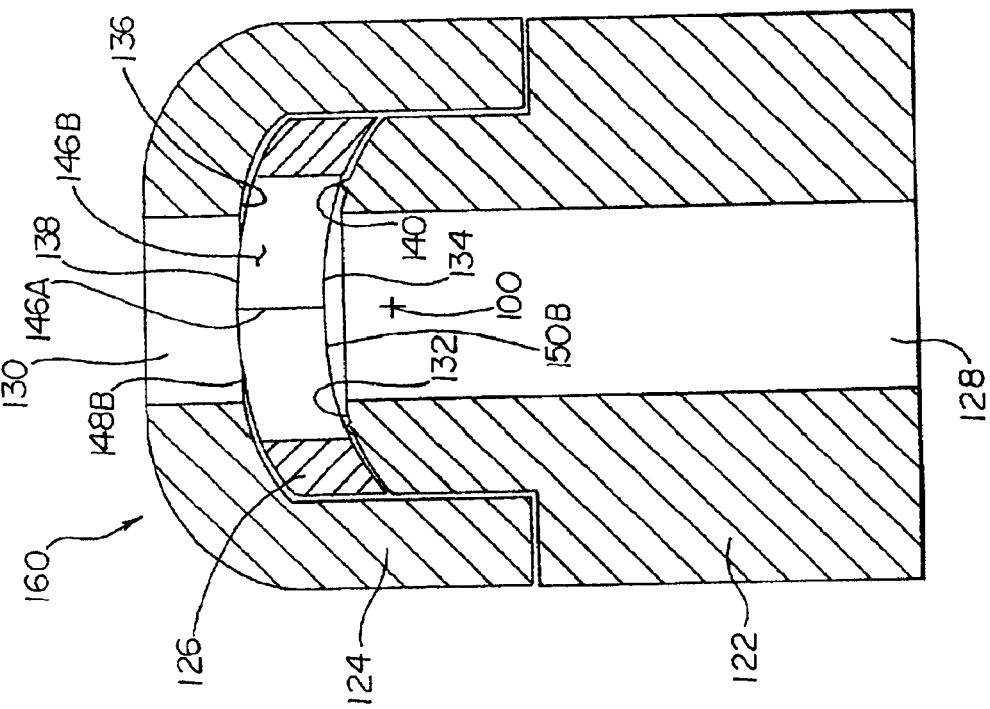

HEMOSTASIS GASKET VALVE

FIELD OF THE INVENTION

The present invention generally relates to introducer sheaths for use in medical procedures requiring vascular access. More specifically, the present invention relates to hemostasis gasket valves for use in introducer sheaths and other medical devices.

BACKGROUND OF THE INVENTION

Vascular introducer sheaths are used in a wide variety of vascular procedures and typically include an introducer sheath having a hemostasis valve which inhibits backbleeding. As a general matter, the prior art provides a number of different hemostasis valve designs which typically vary in terms of the valve shape, slit geometry, slit position, and other design aspects. There is an ongoing need to improve such hemostasis valve designs in terms of providing better hemostasis (i.e., preventing back-bleeding) in the various modes of operation, minimizing drag on devices inserted therethrough, providing increased resistance to pressure and vacuum gradients, providing easy loading of devices, and maximizing safety.

SUMMARY OF THE INVENTION

In an exemplary embodiment of the present invention, these disadvantages are addressed by providing, for example, a vascular introducer sheath having a hemostasis valve assembly including a gasket onto which compressive forces are distributed to avoid puckering of the slit(s) and to provide balanced performance in terms of bi-directional sealing effectiveness and device movement therethrough. Specific embodiments are described in more detail hereinafter.

BRIEF DESCRIPTION OF THE DRAWINGS

FIG. 2A is a cross-sectional side view of a hemostasis valve assembly of the present invention for use with the introducer sheath illustrated in FIG. 1, taken along a plane orthogonal to the slit;

FIG. 2B is a cross-sectional side view of the hemostasis valve assembly illustrated in FIG. 2A, taken along a plane parallel to the slit;

FIG. 5A is a cross-sectional side view of an alternative hemostasis valve assembly of the present invention for use with the introducer sheath illustrated in FIG. 1, taken along a plane parallel to the first slit and orthogonal to the second slit;

FIG. 5B is a cross-sectional side view of the hemostasis valve assembly illustrated in FIG. 5A, taken along a plane orthogonal to the first slit and parallel to the second slit;

DETAILED DESCRIPTION OF THE INVENTION

The following detailed description should be read with reference to the drawings in which similar elements in different drawings are numbered the same. The drawings, which are not necessarily to scale, depict illustrative embodiments and are not intended to limit the scope of the invention.

Figure 1:
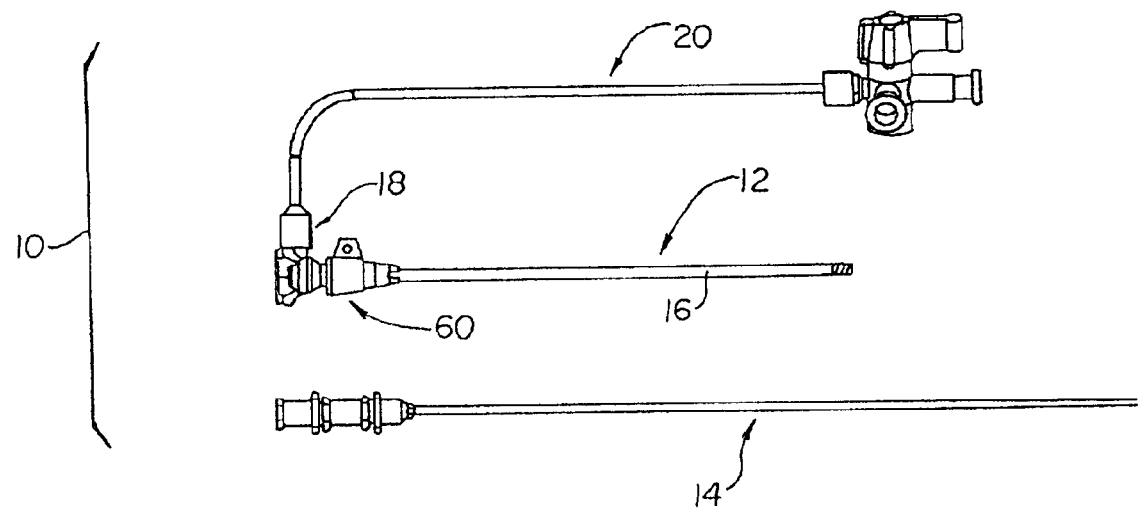
FIG. 1 is a plan view of a vascular access system of the present invention including an introducer sheath and a dilator.

Refer now to FIG. 1 which illustrates a plan view of a vascular access system 10 in accordance with the present invention. Vascular access system 10 includes two primary components, namely an introducer sheath 12 and a dilator 14. Introducer sheath 12 includes an elongate shaft 16 and a hemostasis valve assembly 60. The hemostasis valve assembly 60 is connected to the proximal end of the shaft 16 utilizing conventional techniques. Hemostasis valve assembly 60 includes a hub, a cap and a gasket disposed therebetween as will be described in greater detail with reference to the remaining figures. The hub of the hemostasis assembly 60 may include a side port 18 for connection to a flush or injection tube subassembly 20. By way of example, not limitation, the shaft 16 of the introducer sheath 12 may have a size (outside diameter or profile) ranging from 4F to 16F or larger, and a length ranging from 10 cm to 25 cm or longer. The distal tip of the elongate shaft 16 is preferably tapered to facilitate smooth insertion into the vascular system and smooth transition to the dilator 14.

Refer now to FIGS. 2A and 2B which illustrate cross-sectional side views of the hemostasis valve assembly 60 for use with the introducer sheath 12 illustrated in FIG. 1. As mentioned previously, the hemostasis valve assembly 60 includes a hub 22, a cap 24 and a gasket 26 disposed therebetween. For purposes of simplicity and clarity, the side port 19 of the hub 22 is not illustrated. Similarly, although not illustrated for purposes of simplicity and clarity, the hub 22 and the end cap 24 include a means for compressive connection therebetween, such as a snap-fit connection or a threaded connection, both of which are well-known in the art.

The hub 22 includes an inner lumen 28 extending therethrough, and the end cap 24 includes an aperture 30 extending therethrough. The inner lumen 28 of the hub 22 is in fluid communication with the aperture 30 of the end cap 24 absent the gasket 26, which includes one or more slits 46 as will be discussed in more detail hereinafter. The inner lumen 28 and the aperture 30 accommodate intravascular devices such as catheters, guide wires and the like therein. The hub 22 and the end cap 24 may have conventional dimensions and may be formed of conventional materials using known manufacturing techniques.

Figure 4:
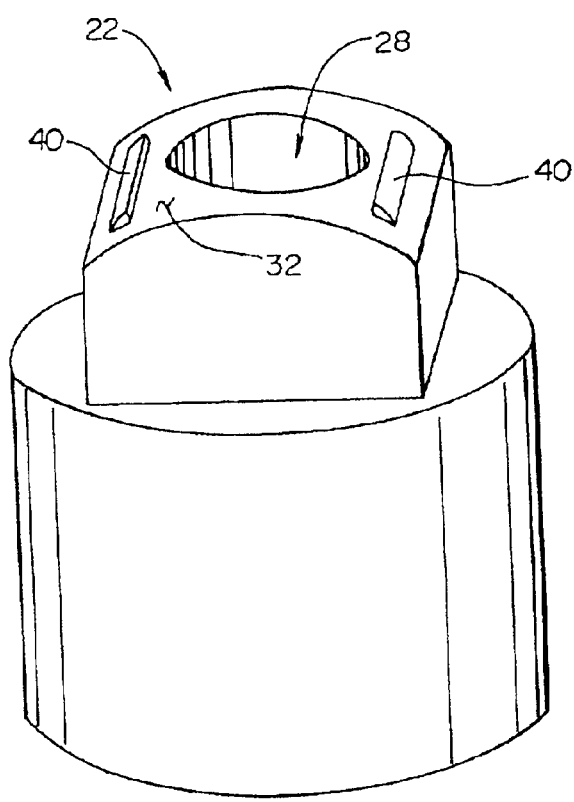
FIG. 4 is an isometric view of the hub used in the hemostasis valve assembly shown in FIGS. 2A and 2B.

Hub 22 includes a contact surface 32 which is in intimate contact with the bottom surface 34 of the gasket 26. Similarly, the end cap 24 includes a contact surface 36 in intimate contact with the top surface 38 of the gasket 26. The contact surfaces 32, 36 may be smooth or include a ridge 40 to assist in imparting curvature to the gasket 26 and to grip the gasket 26. The contact surfaces 32, 36 include both curved portions as seen in FIG. 2A and flat portions as seen in FIG. 2B. FIGS. 2A and 2B are cross-sectional views taken at orthogonal angles to each other. Thus, the curved portions of the contact surfaces 32, 36 are oriented at a right angle to the flat (non-curved) portions of the contact surfaces 32, 36. The orientation of the curved and flat portions of the contact surface 32 of the hub 22 may be readily appreciated from the isometric view of the hub 22 as shown in FIG. 4.

As seen in FIG. 2A, the curved portions of the contact surfaces 32, 36 impart curvature to the gasket 26 about an axis 100, which appears as a point in FIG. 2A. The curvature may be convex as shown, or concave, depending on the direction of curvature of the curved portions of the contact surfaces 32, 36. As seen in FIG. 2B, the flat portions of the contact surfaces 32, 36 hold the gasket flat and parallel to the axis 100, which appears as a line in FIG. 2B. Preferably, the axis 100 is parallel to the slit 46 as discussed in greater detail hereinafter.

The slit 46 of the gasket 26 includes a top edge 48 and a bottom edge 50 as shown in FIG. 2B. By orienting the axis 100 parallel to the slit 46 and by curving the gasket 26 about axis 100 while the remainder thereof remains flat, compressive forces are distributed along the bottom edge 50 of the slit 46 to avoid puckering and provide enhanced sealing, with or without devices inserted therein. Compressive forces may be distributed along the top edge 48 of the slit 46 to have the same effect by changing the direction of curvature of the gasket 26 (i.e., by changing from a convex shape as shown to a concave shape).

Figure 3A:
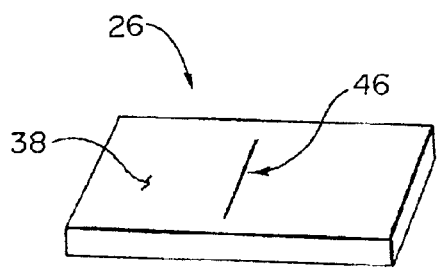
FIG. 3A is an isometric view of the gasket, shown in a flat position, used in the hemostasis valve assembly shown in FIGS. 2A and 2B.
Figure 3B:
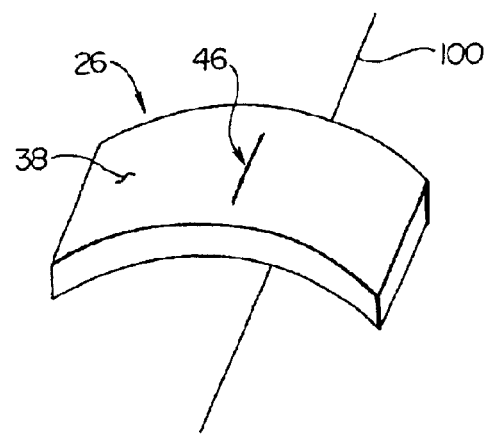
FIG. 3B is an isometric view of the gasket shown in FIG. 3B, but shown in a curved position.

The gasket 26 may be normally flat as shown in FIG. 3A. In response to compression between the hub 22 and the end cap 24, the gasket 26 is curved about axis 100 and the gasket 26 assumes a semi-cylindrical shape as seen in FIG. 3B. The gasket 26 may have a circular outside shape, but preferably has a shape other than round such as an oval, a square or a rectangle as shown. The other-than-round perimeter geometry of the gasket 26 and the corresponding shapes of the recess of the cap 24 and the top portion of the hub 22 aid in aligning the slit 46 parallel to the axis of curvature 100 as defined by the curved portions of the contact surfaces 32, 36.

The gasket 26 may be formed of a variety of elastomeric materials such as PDMS, latex or other suitable material. Preferably, the gasket 26 has a durometer in the range of 15A-50A. The gasket 26 thickness may range from approximately 0.045 to 0.075 inches and may have outside dimensions ranging from 0.050 to 0.500 inches. The thickness of the gasket 26 may be uniform or may vary with a thick portion in the middle and a thin portion around the periphery thereof. The gasket 26 may be punched out of a sheet of elastomeric material or molded using conventional techniques. The slit 46 may be punched through the gasket 26 using a cutter or other suitable means. Those skilled in the art will recognize that the dimensions, materials and methods of manufacture may be readily modified without departing from the scope or spirit of the invention.

Refer now to FIGS. 5A and 5B which illustrate cross-sectional side views of an alternative hemostasis valve assembly 160 of the present invention for use with the introducer sheath 12 illustrated in FIG. 1. Except as described herein or otherwise implicit from the drawings, hemostasis valve assembly 160 is similar in design and use as hemostasis valve assembly 60 described previously.

The hemostasis valve assembly 160 includes a hub 122, a cap 124 and a gasket 126 disposed therebetween. For purposes of simplicity and clarity, the side port 19 of the hub 122 is not illustrated. Similarly, although not illustrated, the hub 122 and the end cap 124 include a means for compressive connection therebetween, such as a snap-fit connection or a threaded connection, both of which are well-known in the art.

The hub 122 includes an inner lumen 128 extending therethrough, and the end cap 124 includes an aperture 130 extending therethrough. The inner lumen 128 of the hub 122 is in fluid communication with the aperture 130 of the end cap 124 absent the gasket 126, which preferably includes two slits 146A and 146B oriented at orthogonal angles as discussed in more detail hereinafter. The inner lumen 128 and the aperture 130 accommodate intravascular devices such as catheters, guide wires and the like therein. The hub 122 and the end cap 124 may have conventional dimensions and may be formed of conventional materials using known manufacturing techniques.

Hub 122 includes a contact surface 32 which is in intimate contact with the bottom surface 134 of the gasket 126. Similarly, the end cap 124 includes a contact surface 136 in intimate contact with the top surface 138 of the gasket 126. The contact surfaces 132, 136 may be smooth or include a ridge 140 to assist in imparting curvature to the gasket 126 and to grip the gasket 126. The contact surfaces 132, 136 include both convex curved portions as seen in FIG. 5A and concave curved portions as seen in FIG. 5B. FIGS. 5A and 5B are cross-sectional views taken at orthogonal angles to each other. Thus, the convex curved portions of the contact surfaces 132, 136 are oriented at a right angle to the concave curved portions of the contact surfaces 132, 136.

As seen in FIG. 5A, the convex curved portions of the contact surfaces 132, 136 impart convex curvature to the gasket 126 about an axis 100, which appears as a point in FIG. 5A. As seen in FIG. 5B, the concave curved portions of the contact surfaces 132, 136 impart concave curvature to the gasket 126 about the axis 200, which appears as a point in FIG. 5B. Preferably, the first axis 100 is parallel to the first slit 146A, and the second axis 200 is parallel to the second slit 146B as most clearly shown in FIG. 6A and discussed in greater detail hereinafter.

The slits 146A and 146B of the gasket 126 each include a top edge 148A and 148B and a bottom edge 150A and 150B, respectively, as shown in FIGS. 5A and 5B. By orienting the first axis 100 parallel to the first slit 146A and the second axis 200 parallel to the second slit 146B, and by curving the gasket 126 about axis 100 in a first direction and curving the gasket 126 about axis 200 in a second (opposite) direction, compressive forces are distributed along the bottom edge 150A of the first slit 146A and the top edge 148B of the second slit 146B, to provide balanced performance in terms of bi-directional sealing effectiveness and device movement therethrough. In other words, the gasket 126 provides the same effective seal and the same reduced drag regardless of the direction of the pressure gradient or the direction of device movement therein.

Figure 6B:
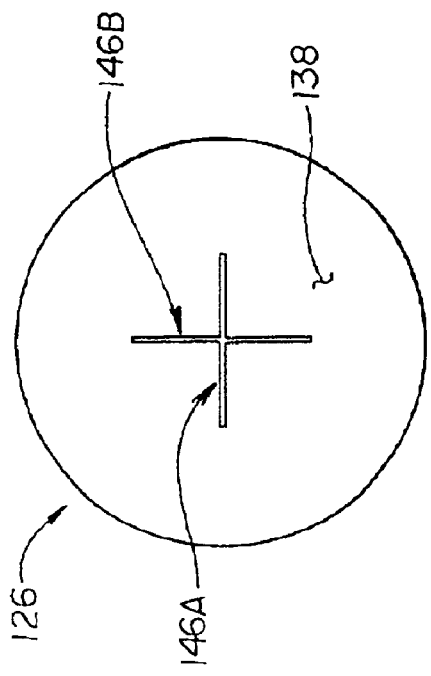
FIG. 6B is a top view of the gasket shown in FIG. 6A.
Figure 6C:
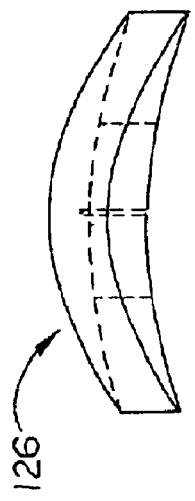
FIG. 6C is a side view of the gasket shown in FIG. 6A.
Figure 6A:
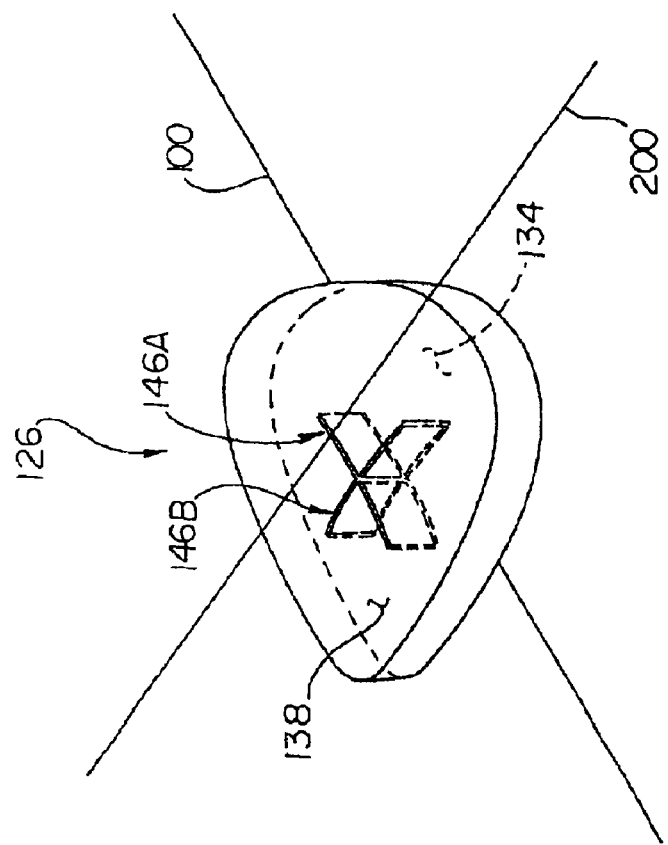
FIG. 6A is an isometric view of the gasket, shown in a curved position, used in the hemostasis valve assembly shown in FIGS. 5A and 5B.

The gasket 126 may be normally flat, and in response to compression between the hub 122 and the end cap 124, the gasket 126 is curved about axes 100 and 200 to cause the gasket 26 to assume a saddle shape as seen in FIG. 6A, having both a concave contour and a convex contour on the same side. Top and side views of the gasket 126 are illustrated in FIGS. 6B and 6C, respectively. The gasket 126 may have a circular outside shape, but preferably has a shape other than round such as an oval, a square or a rectangle as shown. The other-than-round perimeter geometry of the gasket 126 and the corresponding shapes of the recess of the cap 124 and the top portion of the hub 122 aid in aligning the slits 146A and 146B parallel to the axes of curvature 100 and 200 as defined by the convex and concave curved portions of the contact surfaces 132, 136.

Those skilled in the art will recognize that the present invention may be manifested in a variety of forms other than the specific embodiments described and contemplated herein. Accordingly, departures in form and detail may be made without departing from the scope and spirit of the present invention as described in the appended claims.

What is claimed is:

1. A vascular introducer sheath for use with a vascular access system, the vascular introducer sheath comprising:
   a tubular shaft having a proximal end and a distal end;
   a hemostasis valve assembly connected to the proximal end of the tubular shaft, the hemostasis valve assembly including a hub, a cap, and a gasket disposed therebetween, wherein the gasket has one or more slits each having a top edge and a bottom edge, and wherein the hub and the cap distribute compressive forces along one of the top and bottom edges of each slit such that the slits do not pucker; and
   wherein the gasket is curved only along an axis parallel to each slit.

2. A vascular introducer sheath for use with a vascular access system, the vascular introducer sheath comprising:
   a tubular shaft having a proximal end and a distal end;
   a hemostasis valve assembly connected to the proximal end of the tubular shaft, the hemostasis valve assembly including a hub, a cap, and a gasket disposed therebetween, wherein the gasket has one or more slits each having a top edge and a bottom edge, and wherein the hub and the cap distribute compressive forces along one of the ton and bottom edges of each slit such that the slits do not pucker; and
   wherein the gasket has a single slit and wherein the gasket is curved along an axis parallel to the single slit to form a semi-cylindrically shaped gasket.

3. A vascular introducer sheath for use with a vascular access system, the vascular introducer sheath comprising: a tubular shaft having a proximal end and a distal end; a hemostasis valve assembly connected to the proximal end of the tubular shaft, the hemostasis valve assembly including a hub, a cap, and a gasket disposed therebetween, wherein the gasket has one or more slits each having a top edge and a bottom edge, and wherein the hub and the cap distribute compressive forces along one of the top and bottom edges of each slit such that the slits do not pucker, and wherein the gasket has a first slit and a second slit, wherein the gasket is curved in a first direction along an axis parallel to the first slit, wherein the gasket is curved in a second direction along an axis parallel to the second slit, and wherein the first direction is opposite the second direction, and wherein the first slit is orthogonal to the second slit to form a saddle shaped gasket.

4. A vascular introducer sheath for use with a vascular access system, the vascular introducer sheath comprising:
   a tubular shaft having a proximal end and a distal end; and
   a hemostasis valve assembly connected to the proximal end of the tubular shaft, the hemostasis valve assembly including a hub, a cap, and a gasket disposed therebetween, wherein the gasket has one or more slits, and wherein the gasket is curved only along an axis parallel to each slit.

5. A vascular introducer sheath as in claim 4, wherein the gasket has a single slit and wherein the gasket is curved along an axis parallel to the single slit to form a semi-cylindrically shaped gasket.

6. A vascular introducer sheath as in claim 4, wherein the gasket has a first slit and a second slit, wherein the gasket is curved in a first direction along an axis parallel to the first slit, wherein the gasket is curved in a second direction along an axis parallel to the second slit, and wherein the first direction is different than the second direction.

7. A vascular introducer sheath as in claim 6, wherein the first direction is opposite the second direction.

8. A vascular introducer sheath as in claim 7, wherein the first slit is orthogonal to the second slit to form a saddle shaped gasket.

9. A vascular introducer sheath for use with a vascular access system, the vascular introducer sheath comprising:
   a tubular shaft having a proximal end and a distal end; and
   a hemostasis valve assembly connected to the proximal end of the tubular shaft, the hemostasis valve assembly including a hub, a cap, and a gasket disposed therebetween, wherein the gasket has a slit, and wherein the gasket is curved along a single axis to form a semi-cylindrically shaped gasket.

10. A vascular introducer sheath as in claim 9, wherein the gasket is curved along an axis parallel to the slit.

11. A vascular introducer sheath as in claim 9, wherein the gasket is curved along an axis parallel to the slit and is otherwise not curved.

12. A vascular introducer sheath as in claim 9, wherein the gasket has a single slit and wherein the gasket is curved along an axis parallel to the single slit and is flat along an axis orthogonal to the single slit.

13. A vascular introducer sheath as in claim 9, wherein the slit has a bottom edge and a top edge, and wherein compressive forces are distributed along one of the bottom or top edges to avoid slit puckering.

14. A vascular introducer sheath as in claim 9, wherein no compressive forces are distributed perpendicular to the bottom and top edges.

15. A vascular introducer sheath for use with a vascular access system, the vascular introducer sheath comprising:
   a tubular shaft having a proximal end and a distal end; and
   a hemostasis valve assembly connected to the proximal end of the tubular shaft, the hemostasis valve assembly including a hub, a cap, and a gasket disposed therebetween, wherein the gasket is curved in a first direction along an axis, wherein the gasket is curved in a second direction along an axis, and wherein the first direction is different from the second direction to form a saddle-shaped gasket.

16. A vascular introducer sheath as in claim 15, wherein the gasket has a first slit and a second slit, wherein the gasket is curved in the first direction along an axis parallel to the first slit, and wherein the gasket is curved in a second direction along an axis parallel to the second slit.

17. A hemostasis valve assembly for use with a vascular device, the hemostasis valve assembly comprising a hub, a cap, and a gasket disposed therebetween, wherein the gasket has one or more slits each having a top edge and a bottom edge, and wherein compressive forces are distributed along one of the top and bottom edges of each slit such that the one or more slits do not pucker, and wherein the gasket is curved only along an axis parallel to each slit.

18. A hemostasis valve assembly for use with a vascular device, the hemostasis valve assembly comprising a hub, a cap, and a gasket disposed therebetween, wherein the gasket has a side with a concave contour and a convex contour.

19. A hemostasis valve assembly for use with a vascular device, the hemostasis valve assembly comprising a hub, a cap, and a gasket disposed therebetween, wherein the gasket has one or more slits each having a top edge and a bottom edge, and wherein the hemostasis valve assembly includes means for distributing compressive forces along one of the top and bottom edges of each slit such that the one or more slits do not pucker, and wherein the gasket is curved only along an axis parallel to each slit.

* * * * *

UNITED STATES PATENT AND TRADEMARK OFFICE
CERTIFICATE OF CORRECTION

PATENT NO.    : 6,776,774 B2                                              Page 1 of 1
DATED         : August 17, 2004
INVENTOR(S)   : William J. Tansey, Jr. et al.

It is certified that error appears in the above-identified patent and that said Letters Patent is hereby corrected as shown below:

Column 5,
Line 27, delete "ton" and insert therefor -- top --.

Signed and Sealed this

Fourteenth Day of December, 2004

JON W. DUDAS
*Director of the United States Patent and Trademark Office*